United States Patent [19]

Johnston

[11] Patent Number: 4,690,171

[45] Date of Patent: Sep. 1, 1987

[54] VALVE ASSEMBLY FOR A SPHYGMOMANOMETER

[76] Inventor: Charles F. Johnston, Rte. 1, Box 400, Fincastle, Va. 24090

[21] Appl. No.: 870,968

[22] Filed: Jun. 5, 1986

[51] Int. Cl.$^4$ .............................................. F16K 47/08
[52] U.S. Cl. .................................... 137/877; 128/685; 137/625.48; 137/860; 251/297; 251/344
[58] Field of Search .................... 128/685; 137/625.48, 137/860, 877; 251/297, 344

[56] References Cited

U.S. PATENT DOCUMENTS

| | | | |
|---|---|---|---|
| 3,459,217 | 8/1969 | Callahan | 137/860 X |
| 3,823,707 | 7/1974 | Hayes | 128/685 |
| 3,893,478 | 7/1975 | Peters | 128/685 X |
| 4,098,291 | 7/1978 | Clark et al. | 128/685 X |
| 4,146,018 | 3/1979 | Aldridge et al. | 128/685 |
| 4,198,031 | 4/1980 | Ezekiel et al. | |
| 4,200,259 | 4/1980 | Ueda | |
| 4,210,154 | 7/1980 | Klein | |

FOREIGN PATENT DOCUMENTS 2751794  5/1979  Fed. Rep. of Germany ...... 281/297

*Primary Examiner*—Gerald A. Michalsky
*Attorney, Agent, or Firm*—Birch, Stewart, Kolasch & Birch

[57] ABSTRACT

A valve assembly for a sphygmomanometer controls the inflation and deflation of a pressure cuff. The valve assembly includes an inlet connectable to a fluid pressure source such as a bellows, an outlet which is connectable to a blood pressure cuff, an inlet directional control which actively prevents the flow of fluid from the outlet to the inlet, axial passages which connect the inlet to the outlet, and means for slowly and fixedly or rapidly releasing pressure. The valve assembly may be set to one of three positively located positions: a cuff inflation position, a metered deflation position, or a fast vent position. In the cuff inflation position, fluid pressure delivered to the valve assembly's inlet passes through an inlet directional control to the valve assembly's outlet and on to the pressure cuff which becomes inflated. In the metered deflation position, fluid flow returned from the pressure cuff through the outlet is metered out of the valve assembly in order to slowly deflate the pressure cuff at a consistent rate, regardless of the number of different readings or operators. In the fast vent position, fluid flow returned from the pressure cuff through the outlet is directed through large exhaust openings so that the pressure cuff can be rapidly deflated.

10 Claims, 4 Drawing Figures

4,690,171

VALVE ASSEMBLY FOR A SPHYGMOMANOMETER

BACKGROUND OF THE INVENTION

The present invention relates to a sphygmomanometer and, more particularly, to a valve assembly for a sphygmomanometer which controls the inflation and deflation of a pressure cuff.

Traditionally, sphygmomanometers measure blood pressure through the use of a bellows which forces air or other fluid through a valve assembly to inflate a pressure cuff. Blood pressure is measured by slowly decreasing the pressure in the pressure cuff (deflating the pressure cuff) and noting the pressures at which sounds characteristic of systolic and diastolic pressures are heard by an operator using a stethoscope. Conventionally, this cuff inflation and the slow decrease in pressure is controlled by the valve assembly, which allows air or other fluid flowing back from the pressure cuff to slowly be metered out of the valve assembly.

Generally, these valve assemblies provide a positional mechanism for the release of pressure from the pressure cuff. Normally, there is a fast vent position, for rapidly deflating the pressure cuff after systolic and diastolic pressures have been determined, and a metered deflation position, for slowly deflating the pressure cuff while systolic and diastolic pressure measurements are being taken. The fast vent and metered deflation positions, usually, are manually set, often requiring considerable manual dexterity or two-handed manipulation. Setting positions for the pressure release mechanism are normally variable with no way to positively locate the fast vent and metered deflation positions, hence, the metering rate may vary from reading to reading and from operator to operator, thereby creating inconsistencies in blood pressure measurements.

Additionally, conventional valve assemblies often use spring devices or disc type devices as check valves to prevent the leakage of air or other fluid from the pressure cuff back into the bellows. These devices do not provide a positive shut off of the air or other fluid flow other than by fluid force. Therefore, some leakage into the bellows may occur. This leakage detracts from the efficiency of cuff inflation and the consistency of blood pressure measurements. Furthermore, these conventional check valves may require the application of significant pressure to be opened such that air or other fluid may flow from the bellows to the pressure cuff. As a result, the efficiency of cuff inflation may be hindered.

Accordingly, it would be desirable to provide a valve assembly for a sphygmomanometer which would allow more consistent blood pressure measurements to be taken while eliminating the need for manual dexterity in setting the pressure release mechanism, thereby, enhancing medical industry standards and making it easier for laymen to take accurate blood pressure measurements.

SUMMARY OF THE INVENTION

Accordingly, it is a primary object of the invention to provide a valve assembly for a sphygmomanometer which allows the operator to positively locate the cuff inflation, fast vent and metered deflation positions of the valve assembly in order to obtain similar rates of pressure reduction of a pressure cuff from reading to reading and operator to operator.

It is a further object of the present invention to provide a valve assembly for a sphygmomanometer which uses a positive shut off check valve to prevent fluid flow back into the bellows or other fluid pressure producing device without requiring the application of significant pressure to open the check valve so that fluid flow may proceed from the bellows or other fluid pressure producing device to the pressure cuff, thereby, improving the efficiency and consistency of pressure cuff inflation and deflation.

It is another object of the present invention to provide a valve assembly for a sphygmomanometer which does not require considerable manual dexterity or two-handed manipulation to initiate the reduction of pressure in the pressure cuff and which may be manufactured at a reasonable cost.

Additionally, it is an object of the present invention to provide a precision metering mechanism, for the metered deflation of a pressure cuff, which will not become clogged by the collection of particles.

It is a further object of the present invention to provide a valve assembly which includes a directional control device configured so as to ensure an air tight seal even in the presence of airborne contaminants.

These and other objects of the present invention are accomplished by providing a valve assembly for a sphygmomanometer comprising an inlet connectable to a device which provides fluid pressure such as a bellows, an outlet connectable to a pressure cuff, a directional control device which allows air or other fluid to pass from the inlet to the outlet with the application of a low pressure but positively shuts off the flow of air or other fluid from the outlet back into the inlet, a metering mechanism which allows air or other fluid flowing back from the outlet to be metered at a precise and fixed rate to slowly deflate the pressure cuff without becoming clogged, a fast vent mechanism for rapidly deflating the pressure cuff, and a three position valve mechanism which allows the user to positively locate and select single handedly and without considerable manual dexterity a cuff inflation position, wherein fluid flow is provided from the inlet through the directional control device and into the outlet, a metered deflation position, wherein air or other fluid returned through the outlet is provided to the metering mechanism, and a fast vent position, wherein air or other fluid returned through the outlet is provided to the fast vent mechanism.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF DRAWINGS

The present invention will become more fully understood from the detailed description given hereinbelow and the accompanying drawings which are given by way of illustration only, and thus are not limitative of the present invention and wherein.

DETAILED DESCRIPTION OF THE PREFERRED EMBODIMENT

Figure 1:
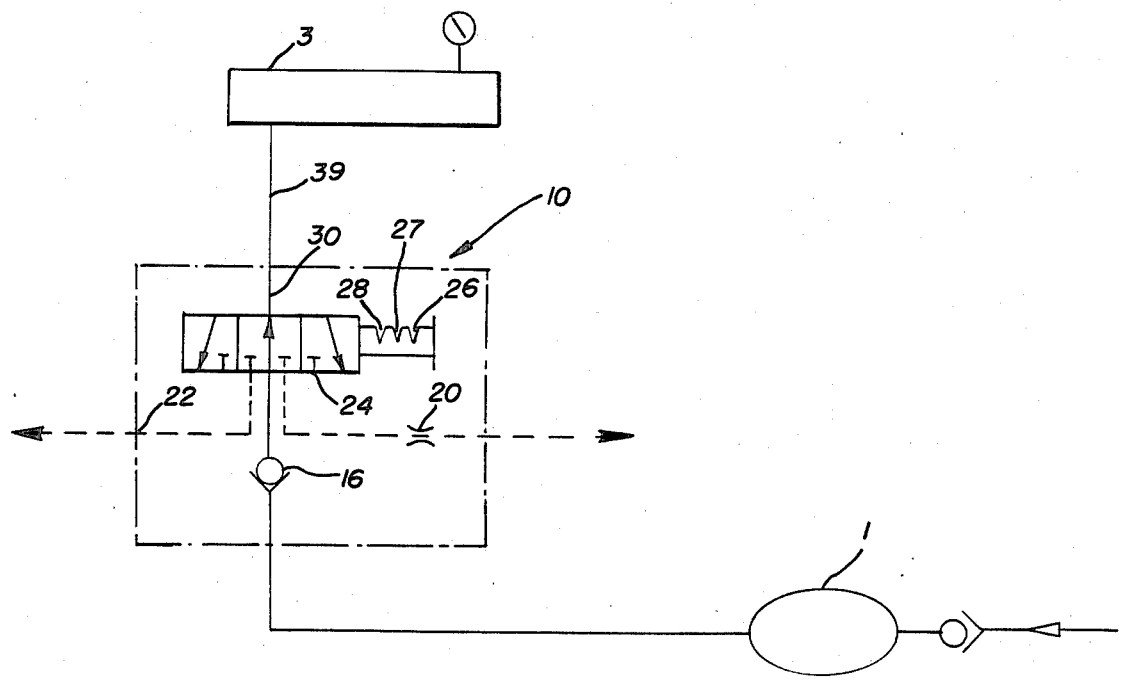
FIG. 1 is a schematic view of a sphygmomanometer with a valve assembly according to a preferred embodiment of the present invention.

FIG. 1 is a schematic view of a sphygmomanometer with a valve assembly (generally indicated as 10) configured according to a preferred embodiment of the present invention. The valve assembly 10 is connected to a bellows 1, which provides fluid pressure to the valve assembly 10, and a pressure cuff 3, which may be inflated or deflated by the valve assembly 10. At opposite ends of the valve assembly 10 are an outlet 30, connected to a pressure supply hose 39 which is connected to the pressure cuff 3, and an inlet check valve 16, which is connected to the bellows 1 and provides for the one way directional flow of air into valve assembly 10 from bellows 1. While any other fluid might be used within the scope of the present invention, the present preferred embodiment utilizes air as the operative fluid.

The valve assembly 10 contains a fixed air bleed orifice assembly 20, for metering the flow of air returned through the outlet 30 thereby slowly deflating the pressure cuff 3, and a fast vent opening 22, for rapidly deflating the pressure cuff 3. Valve assembly 10 also contains a three position valve mechanism 24 which enables a user to select between the cuff inflation position, the metered deflation position, and the fast vent position. The valve mechanism 24 contains first, second and third detent grooves 26, 27, and 28, which allow a user to positively locate each of the three above described positions.

Figure 2:
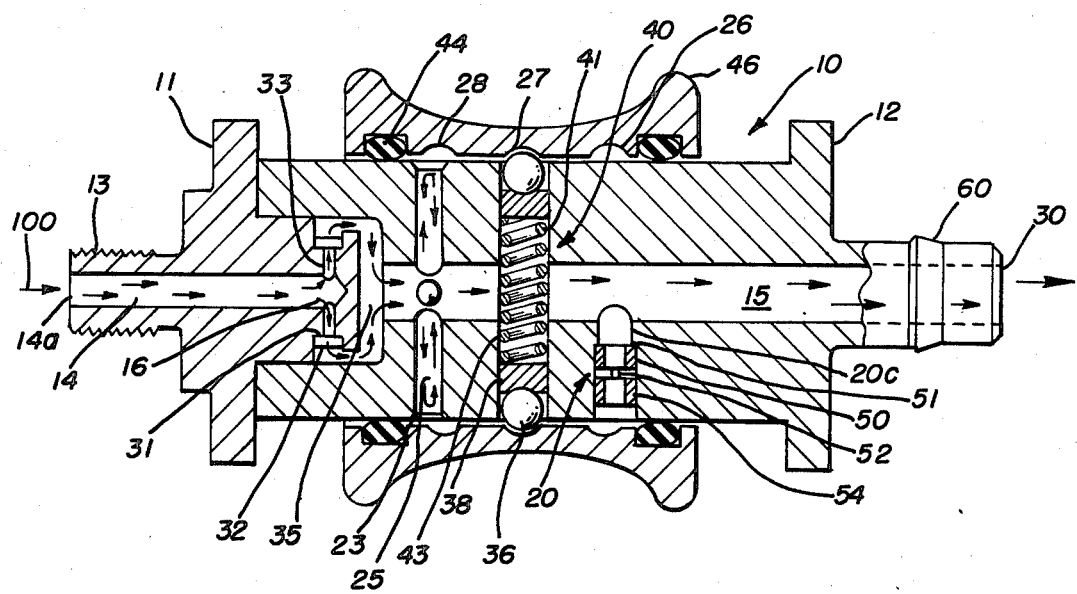
FIG. 2 is a sectional view of a valve assembly according to a preferred embodiment of the present invention which illustrates the cuff inflation position.
Figure 3:
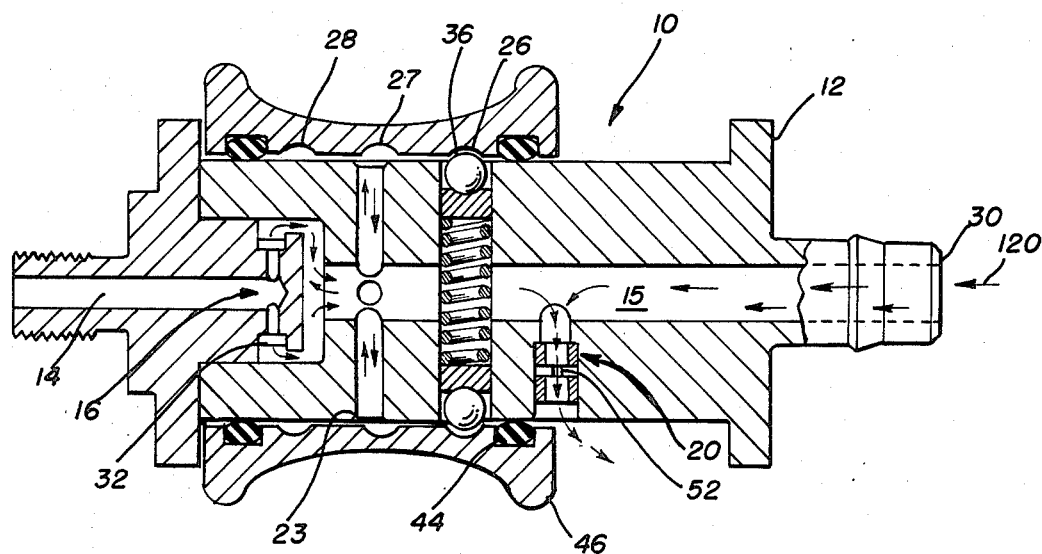
FIG. 3 is a sectional view of the valve assembly of FIG. 2 illustrating the metered deflation position.
Figure 4:
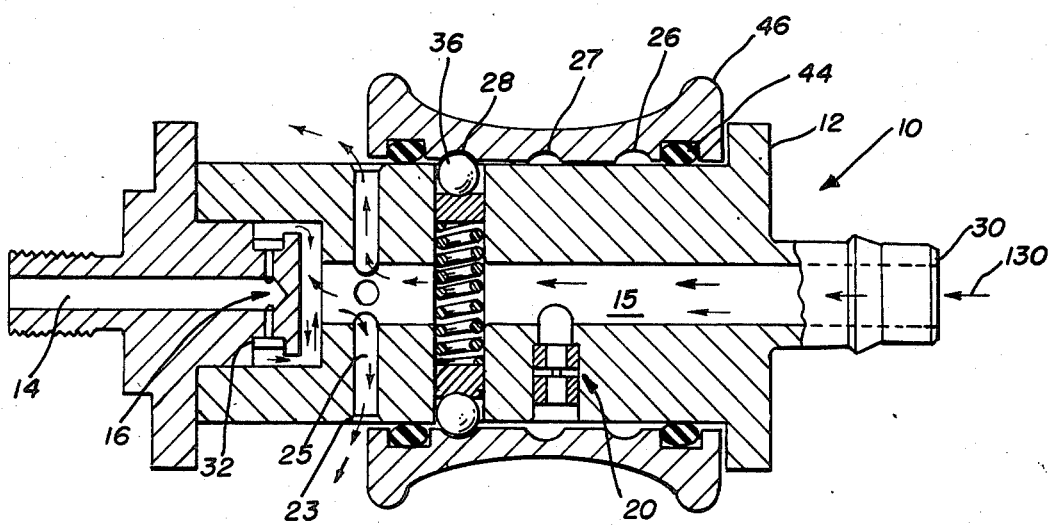
FIG. 4 is a sectional view of the valve assembly of FIG. 2 illustrating the fast vent position.

FIGS. 2, 3, and 4 show sectional views of the valve assembly 10 in the cuff inflation position, the metered deflation position, and the fast vent position, respectively. Referring to FIG. 2, there is shown a valve body 12, of the valve assembly 10, which is generally cylindrical in shape with axial passages running from an inlet 14a to the outlet 30. The inlet passage 14 is provided as an axial passage within an inlet cap 11 which is generally cylindrical in shape and is provided with an inlet nozzle 13 which may be threaded to connect to bellows 1 to, for example, provide a retrofit for existing sphygmomanometers. The inlet nozzle 13 could also utilize a barbed flange to facilitate connection to hose or bulb fittings. The inner end of the inlet cap 11 is provided with an inlet check valve (generally indicated as 16) which is provided in a check valve cavity 35 and which includes an annular check valve recess 31 having a rectangular cross sectional shape and receiving a rectangular rubber valve seal 32 which is substantially conformally configured in cross section. A pair of radial passages 33 are provided for communication between the inlet passage 14 and the annular check valve recess 31. The rectangular rubber valve seal 32 has a resiliency sufficient to allow its displacement away from the radial passages 33 at a pressure easily developed by the bellows 1. This rectangular cross section further ensures that an airtight seal will exist even if airborne particles work between the valve seal 32 and the surface of valve recess 31. When the pressure is applied to the inlet check valve 16 from the outlet 30, however, the seal 32 is pressed against the radial passages 33 to form an air tight seal.

The check valve recess cavity 35 is connected to a central passage 15 axially provided in the valve body 12. A pair of pressure dump passages 25 extend orthagonally from the central passages 15 and intersect therewith. These pressure dump passages terminate with large pressure dump openings 23 at the exterior of valve body 12. A fixed air bleed orifice assembly (generally indicated as 20) is also provided in the valve body 12 and orthagonally extends from and is connected to the central passage 15. The fixed orifice assembly 20 is provided in an orifice receiving cavity 20c which is cylindrically shaped and extends radially from the central passage 15 to the exterior of the valve body 12. The fixed orifice assembly 20 includes a bottom orifice retainer 50 which is securely pressed against an orifice retainer seat 51. A precision orifice 52 is positioned in the orifice receiving cavity 20c over the bottom orifice retainer 50, and a top orifice retainer 54 is pressed in the orifice receiving cavity. The precision orifice 52 is configured as a planar disc provided with a precision sized round orifice having a thin knife-like edge. This configuration allows particles to pass through the orifice without partially clogging the orifice because particles will not collect in corners or on the knife-like edge. The precision orifice 52 may be precision jeweled, precision punched, or molded around a hollow core. The above construction of the precision orifice 52 offers precise metering with reasonable manufacturing costs.

The central passage 15 terminates in the valve outlet 30. The outlet 30 is surrounded by a barbed flange 60 to facilitate secure connection to the pressure supply hose 39 which is connected to the blood pressure cuff 3, as shown in FIG. 1.

An annular sleeve slide 46 is slideably mounted around the exterior of the valve body 12. An O-ring seal 44 is provided at each end of sleeve slide 46 to prevent flow exhaust between the sleeve slide 46 and the exterior surface of the valve body 12. Annular groove detents 26–28 are equispaced about the inner surface of the sleeve slide 46.

A spring detent assembly (generally indicated as 40) includes a spring detent radial passage 41 which extends radially through the valve body 12 and intersects the central passage 15. A force transmitting piston 38 is provided at each exterior end of a common spring 43. A detent ball 36 is provided in the spring detent radial passage 41 outboard of each force transmitting piston 38. Each detent ball 36 is biased by the common spring 43 outwardly from the exterior of valve body 12, against the inner surface of the annular sleeve slide 46 in communication with the detent grooves 26, 27, or 28 of the annular sleeve slide 46.

FIG. 2 illustrates the operation of valve assembly 10 when the annular sleeve slide 46 is positioned so that detent ball 36 cooperates with the second detent groove 27. In this position, the annular sleeve slide 46 covers pressure dump openings 23 and fixed orifice assembly 20. This is the cuff inflation position and facilitates unidirectional flow from the inlet 14a to the outlet 30.

FIG. 3 illustrates the operation of valve assembly 10 when the annular sleeve slide 46 is positioned so that detent ball 36 cooperates with the first detent groove 26. In this position, the annular sleeve slide 46 covers pressure dump openings 23, but not fixed orifice assembly 20. This is the metered deflation position where flow from the outlet 30 is precisely vented to the atmosphere at a metered rate by the fixed orifice assembly 20.

FIG. 4 illustrates the operation of valve assembly 10 when the annular sleeve slide 46 is positioned so that detent ball 36 cooperates with the third detent groove 28. In this position, fixed orifice assembly 20 is covered, but pressure dump openings 23 are uncovered. This is the fast vent position which quickly vents flow from the outlet 30 to the atmosphere.

DESCRIPTION OF OPERATION

In operation, the device of the present application operates as follows. To inflate the pressure cuff 3, the operator using the valve assembly 10 connected to the pressure cuff 3, as shown in FIG. 1, simply slides the annular sleeve slide 46 into the positively locatable cuff inflation position, as shown in FIG. 2, wherein the detent ball 36 cooperates with the second detent groove 27. Common spring 43 balances the detent forces so that the annular sleeve slide 46 may easily be moved forward or backward with a finger or thumb thereby making it easier for laymen to take accurate blood pressure measurements.

In the cuff inflation position, the pressure dump openings 23 and the fixed air bleed orifice assembly 20 are covered by the annular sleeve slide 46. The O-ring seals 44 prevent the exhaust of air from between the annular sleeve slide 46 and the exterior surface of the valve body 12.

Fluid pressure is delivered to the valve inlet 14a by an external fluid pressure source such as the bellows 1, shown in FIG. 1. Delivery of a relatively low pressure forces the rubber valve seals 32 of inlet check valve 16 to open and allow fluid flow into the central passage 15. The rubber valve seals 32 of inlet check valve 16 also act as a positive shut-off to prevent fluid flow from the central passage 15 back into the inlet passage 14 thereby increasing cuff inflation efficiency.

Since the pressure dump openings 23 and the fixed air bleed orifice assembly 20 are completely blocked by the annular sleeve slide 46 and the O-ring seals 44 in this position, the fluid pressure delivered to inlet 14a will proceed through inlet check valve 16 into the central passage 15 to the outlet 30 and on to the pressure cuff 3 which will be inflated as a result of the pressure increase. Flow arrows 100, shown in FIG. 2 illustrate the flow of air through the valve assembly 10 in the cuff inflation position.

To slowly deflate the pressure cuff, the operator can simply slide the annular sleeve slide 46 into the positively locatable metered deflation position, shown in FIG. 3, wherein the detent ball 36 cooperates with the first detent groove 26.

In the metered deflation position, the pressure dump openings 23 are blocked by the annular sleeve slide 46 and the O-ring seals 44, which prevent the escape of air from between the annular slide sleeve 46 and the exterior surface of the valve body 12, with the rubber valve seals 32 of inlet check valve 16 preventing fluid flow from the central passage 15 back into the inlet passage 14. The fixed air bleed orifice assembly 20, however, is uncovered. Fluid pressure returned through the outlet 30 into the central passage 15, therefore, is released only through the fixed air bleed orifice assembly 20. The precision orifice 52 within fixed orifice assembly 20, acts to vent the fluid flow from the outlet 30 at a metered rate without becoming partially clogged by particles, thereby, causing the pressure cuff 3 connected to the outlet 30, as shown in FIG. 1, to be slowly deflated at a fixed and precise rate. Flow arrows 120, shown in FIG. 3, illustrate the flow of air from the outlet 30 through the fixed orifice assembly 20, in the metered deflation position. Because the release of pressure is achieved only by the metered release of pressure through fixed air bleed orifice assembly 20 and the metered deflation position can easily be positively located by the operator, the rate of deflation will be virtually identical for each blood pressure reading and the consistency of blood pressure measurements will be improved.

To rapidly deflate the pressure cuff 3, annular sleeve slide 46 is slid into the positively locatable fast vent position, shown in FIG. 4, wherein the detent ball 36 cooperates with the third detent groove 28. In the fast vent position, pressure dump openings 23 are uncovered. Rubber valve seals 32 of the inlet check valve 16 again prevent fluid flow from the central passage 15 back into the inlet passage 14 and the annular sleeve slide 46 with its O-ring seals 44 prevents the escape of air through fixed orifice assembly 20 by blocking the exhaust of air from between the annular slide sleeve 46 and the exterior surface of the valve body 12. Fluid pressure is released through the large pressure dump openings 23 causing rapid pressure reduction and deflation of pressure cuff 3. Flow arrows 130, shown in FIG. 4, illustrate the flow of air from the outlet 30 through the pressure dump passages 25, and out the pressure dump openings 23, in the quick vent position.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A valve assembly for a sphygmomanometer comprising:
    (a) an inlet connectable to a fluid pressure source;
    (b) an outlet connectable to a pressure cuff;
    (c) inlet directional control means for preventing fluid flow from said pressure cuff to said inlet;
    (d) metering means for metering the fluid flow from said pressure cuff at a fixed rate to control the deflation of said pressure cuff, said metering means having an orifice which provides a fixed flow throughout a metered deflation operation;
    (e) quick vent means for rapidly deflating said pressure cuff; and
    (f) a positively selectable valve selectively directing fluid flow from said inlet to said outlet through said inlet directional control means in a preset cuff inflation position, directing fluid flow from said outlet through said metering means in a preset metered deflation position during a metered deflation operation, or directing fluid flow from said outlet through said quick vent means in a preset quick vent position, said valve means including means for positively retaining said valve in a selected one of said cuff inflation position, said metered deflation position or said fast vent position.

2. The valve assembly of claim 1, wherein said metering means includes a relatively planar disc having a round orifice therethrough, said orifice being provided with a relatively thin knife-like edge.

3. The valve assembly of claim 1 wherein said means for positively securing includes an annular sleeve slide slideably mounted to an exterior surface of a valve body with detent grooves about the inner surface of said annular sleeve slide, said annular sleeve slide being movable over a spring detent means for positively locating said cuff inflation position, said metered deflation position, and said quick dump position.

4. The valve assembly of claim 3, wherein said annular sleeve slide includes O-ring seals provided at each end of said annular sleeve slide to prevent fluid flow exhaust between said annular sleeve slide and said exterior surface of said vlave body.

5. The valve assembly of claim 3, wherein said spring detent means includes a common spring provided with a force transmitting piston at each exterior end of said common spring and a detent ball at each exterior end of said force transmitting pistons.

6. The valve assembly of claim 1, wherein said inlet directional control means includes a rubber valve seal having a resiliency sufficient to allow its displacement at a relatively low pressure in the direction from said inlet to said outlet, but providing an airtight seal in the direction from said outlet to said inlet.

7. The valve assembly of claim 6, wherein said rubber valve seal is rectangular in cross section.

8. The valve assembly of claim 6, wherein said inlet directional control means further includes an annular recess having a rectangular cross section receiving said rubber valve seal, said rubber valve seal having a cross section substantially conformally configured to the cross section of said annular recess.

9. The valve assembly of claim 1 wherein said quick vent means includes a pair of relatively large pressure dump openings.

10. The valve assembly of claim 1 wherein said metering means includes a fixed orifice having a constant orifice area.

* * * * *